United States Patent [19]
Perriard

[11] Patent Number: 6,107,881
[45] Date of Patent: Aug. 22, 2000

[54] ELECTRONIC INTERFACE CIRCUIT BETWEEN A PIEZOELECTRIC TRANSDUCER AND A CIRCUIT FOR PROCESSING A MEASURING SIGNAL PROVIDED BY THE TRANSDUCER

[75] Inventor: Jacques Perriard, Romont, Switzerland

[73] Assignee: Vibro-Meter SA, Switzerland

[21] Appl. No.: 09/311,535

[22] Filed: May 13, 1999

[30] Foreign Application Priority Data

Jun. 16, 1998 [EP] European Pat. Off. .............. 98810546

[51] Int. Cl.[7] .............................. H03F 1/00; H03F 13/00
[52] U.S. Cl. ........................... 330/174; 330/69; 330/258; 327/563; 73/584; 73/632
[58] Field of Search ............................ 330/69, 174, 258; 327/563, 561, 560; 73/587, 584, 632, 570

[56] References Cited

U.S. PATENT DOCUMENTS

| | | | |
|---|---|---|---|
| 3,982,425 | 9/1976 | McLain | 73/632 |
| 4,393,347 | 7/1983 | Looper | 330/258 |
| 4,979,218 | 12/1990 | Strahm | 330/258 |
| 5,220,836 | 6/1993 | Harms et al. | 73/702 |
| 5,339,285 | 8/1994 | Straw | 367/135 |
| 5,371,469 | 12/1994 | Anderson | 324/705 |
| 5,856,891 | 1/1999 | Ngo | 330/258 |

*Primary Examiner*—Michael B Shingleton
*Attorney, Agent, or Firm*—Ostrolenk, Faber, Gerb & Soffen, LLP

[57] ABSTRACT

An electronic circuit serving as an interface between a piezoelectric transducer and a circuit for processing a measuring signal provided by said transducer, said electronic interface circuit serving for providing a constant direct current to said piezoelectric transducer, and for pre-processing an electric signal provided by the transducer via a voltage modulator, said electronic interface circuit being connected to said voltage modulator by a cable having two terminals at each end, the two terminals at a first end of the cable being connected to the output of the voltage modulator and the two terminals at a second end of the cable being connected to said electronic interface circuit. In order to eliminate the error signals caused in particular by common mode interference voltages ("frame voltage"), said electronic interface circuit is characterized in that it comprises (a) a first direct current source for providing a first constant current to said transducer through an electric current loop; (b) a second direct current source for absorbing a second constant current returning from said transducer to said electronic circuit through said loop while said transducer is supplied with said first current; (c) one or a plurality of passive elements allowing to absorb the difference between said first constant current and said second constant current.

6 Claims, 5 Drawing Sheets und 6,107,881

ELECTRONIC INTERFACE CIRCUIT BETWEEN A PIEZOELECTRIC TRANSDUCER AND A CIRCUIT FOR PROCESSING A MEASURING SIGNAL PROVIDED BY THE TRANSDUCER

FIELD OF THE INVENTION

The present invention relates to an electronic circuit serving as an interface between a piezoelectric transducer and a circuit for processing a measuring signal provided by said transducer, said electronic interface circuit serving for supplying a constant direct current to said piezoelectric transducer and for pre-processing an electric signal provided by the transducer via a voltage modulator, said electronic interface circuit being connected to said voltage modulator by a cable having two terminals at each end, the two terminals at a first end of the cable being connected to the output of the voltage modulator and the two terminals at a second end of the cable being connected to said electronic interface circuit.

BACKGROUND OF THE INVENTION

Piezoelectric transducers are e.g. used for the measurement of the vibrations of a machine. To this end, the housing of the transducer is fixed to the machine, and the electric signals provided by the transducer, which signals are representative of the vibrations of the machine, are transmitted by a cable to an electronic circuit for processing a measuring signal provided by the transducer. The latter circuit may by very distant from the transducer. In a measuring chain of this kind, common mode interference potentials, also called "frame voltages" and often designated by Uframe, appear between the housing of the transducer and the ground (zero volt level) of the electronic circuit for processing a measuring signal and generate an error voltage which is superimposed upon the measuring signal provided by the transducer. Furthermore, an additional error signal may result from the fact that the shield of the connecting cable conducts a current caused by the voltage Uframe, such a current flowing between the housing of the piezoelectric transducer and the housing of the electronic circuit for processing of the measuring signal. Moreover, electromagnetic interference may also induce a considerable error signal at the input of the electronic circuit for processing the measuring signal. Known arrangements for the reduction of the different error signals are not efficient enough or relatively expensive.

SUMMARY OF THE INVENTION

It is therefore a main aim of the present invention to provide an electronic interface circuit which allows to prevent, in an effective manner and at a relatively low cost, the superposition of the different above-mentioned error signals to the measuring signal transmitted to the electronic circuit for processing the measuring signal. Therefore, the operating characteristics of such an electronic interface circuit should make possible to build a measuring chain which is capable of:

1) preventing that the presence of a common mode voltage (frame voltage) appearing between the housing which holds the piezoelectric transducer and the housing which holds the electronic circuit that processes the measuring signal may generate an error voltage superimposed upon the measuring signal at the output of said circuit;
2) ensuring that the shield of the connecting cable cannot conduct a current between the housing of the piezoelectric transducer and the housing of the electronic circuit that processes the measuring signal;
3) providing an advantageous behavior of the measuring chain with respect to electromagnetic interferences.

According to the invention, these aims are attained by an electronic interface circuit (EIC) comprising (a) a first direct current source for providing a first constant current to said transducer through an electric current loop;
(b) a second direct current source for absorbing a second constant current returning from said transducer to said electronic circuit through said loop while said transducer is supplied with said first current;
(c) at least one passive element allowing to absorb the difference between said first constant current and said second constant current.

The main advantages of an electronic interface circuit (EIC) of this kind are that it makes possible to build a measuring chain fulfilling above-mentioned requirements 1) to 3), and that it does not need a transformer, which is bulky and relatively expensive, for D.C. decoupling of the electronic circuit connected to the transducer from the electronic circuit for processing the measuring signal.

BRIEF DESCRIPTION OF THE DRAWINGS

Some examples of preferred embodiments of the invention are described in detail hereinafter with reference to the accompanying drawings.

DETAILED DESCRIPTION OF PREFERRED EMBODIMENTS OF THE INVENTION

Figure 1:
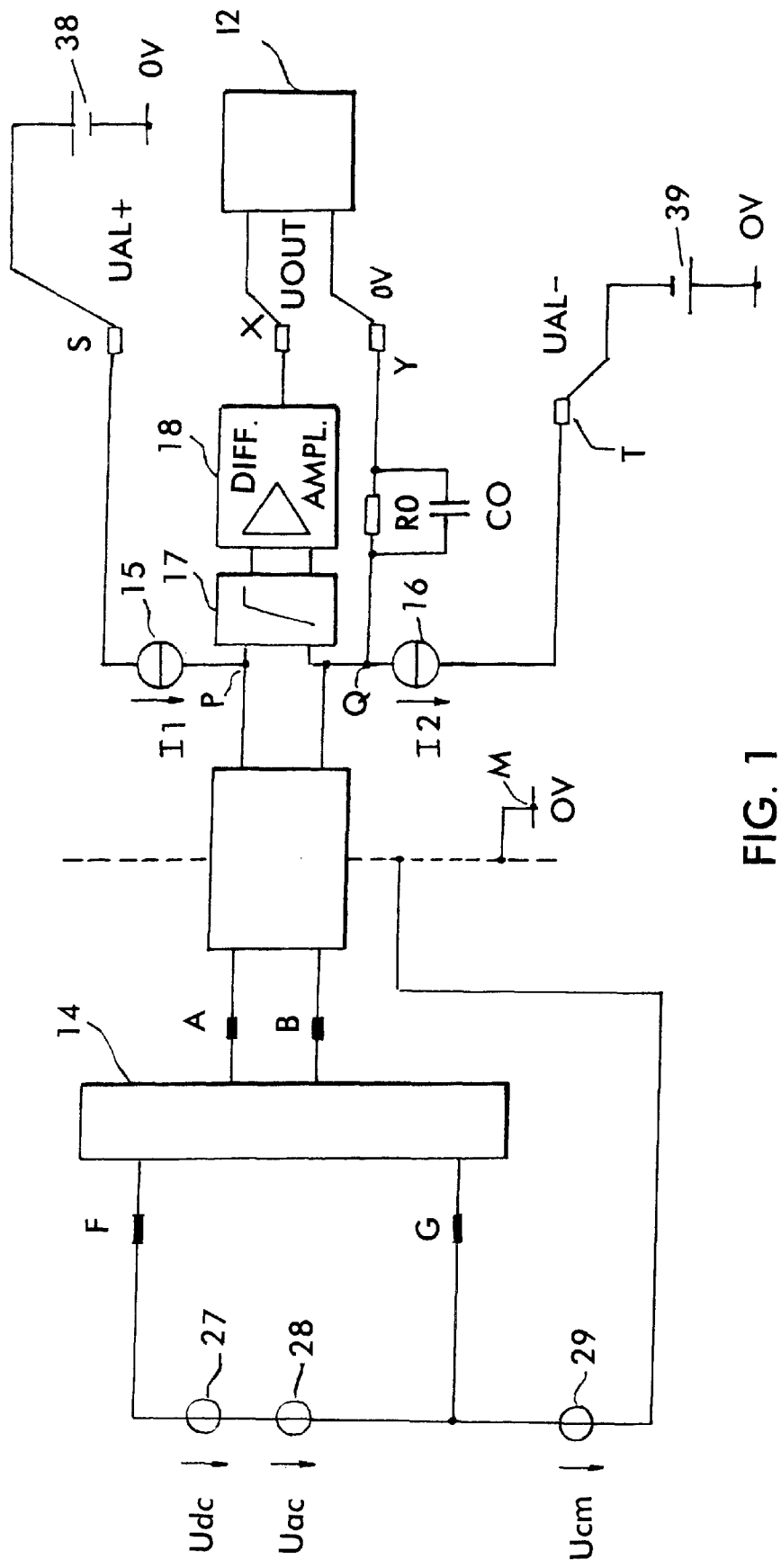
FIG. 1 shows a basic circuit diagram of an electronic circuit according to the invention serving as an interface between a measuring circuit comprising a piezoelectric transducer 11, symbolically represented by voltage sources 27 and 28, and a circuit 12 for processing a measuring signal provided by the transducer.

FIG. 1 shows the basic circuit diagram of an electronic interface circuit according to the invention serving as an interface between a measuring circuit comprising a piezoelectric transducer and a circuit 12 for processing a measuring signal provided by the transducer. In the following description, the electronic interface circuit according to the invention is designated by the abbreviation EIC, and circuit 12 is simply called reading circuit 12 although its function is not necessarily limited to the process of reading the measuring signal.

As described in more detail hereinafter with reference to FIGS. 2 to 4, a measuring circuit comprising a piezoelectric transducer 11 having an electronic circuit 13 integrated therewith is accommodated in a housing 25. A measuring circuit of this kind is symbolically represented in FIG. 1 by the serial connection of a D.C. voltage source 27 delivering a D.C. voltage Udc and of an A.C. voltage source 28 delivering a voltage Uac. Voltage source 29 represents an interference voltage Ucm, i.e. a common mode voltage resulting from the above-mentioned Uframe voltage. As shown in FIG. 1, the just described measuring circuit is connected to the remainder of the system represented in FIG. 1 by means of a cable which is symbolically represented by box 14.

As described in detail hereinafter by means of FIGS. 2 to 4, an EIC according to the invention serves for providing a constant direct current to the piezoelectric transducer, for pre-processing an electric signal provided by the transducer via an electronic circuit comprising e.g. a voltage modulator having a high input impedance, and for providing the pre-processed signal to reading circuit 12. The EIC according to the invention is connected to the piezoelectric transducer by a cable 14. The EIC according to the invention and reading circuit 12 are incorporated in a housing 26 which is represented in FIG. 1 by a dotted line. Housing 26 is connected to the ground M of the EIC, i.e. it is at a voltage level which represents a voltage level of zero volts for the EIC according to the invention and for reading circuit 12 connected thereto.

As shown in FIG. 1, the basic structure of an EIC according to the invention comprises
- a first direct current source 15,
- a second direct current source 16, and
- a passive element, e.g. an impedance Zo, which is connected in parallel between current input terminal Q of the second direct current source 16 and ground M (voltage level 0 volts) of the EIC.

In a preferred embodiment, an EIC according to the invention further comprises
- a high-pass filter 17 serving to receive an electric signal provided by said piezoelectric transducer, and
- a differential amplifier stage 18.

First direct current source 15 provides transducer 11 a first constant current I1 through an electric current loop. A terminal S of current source 15 is connected to the positive terminal of a D.C. voltage source 38 which provides a voltage UAL+.

Second direct current source 16 absorbs a second constant current I2 returning from transducer 11 to said electronic circuit through said loop while transducer 11 is supplied with first current I1. A terminal T of current source 16 is connected to the negative terminal of a D.C. voltage source 39 which provides a voltage UAL−.

The current loop comprises current source 15, terminal P, the circuit connected to terminals P, Q, comprising the piezoelectric transducer, terminal Q, and current source 16.

Impedance Zo is composed of an electric resistor Ro connected in parallel with a capacitor Co. The difference between the two currents I1, I2 is absorbed by Zo.

In a preferred embodiment of an EIC according to the invention, the circuit is designed and dimensioned in such a manner that I1 is very close to I2, so that the voltage appearing across Ro is as low as possible. In practice, there is always a small difference between I1 and I2 on account of tolerances of the components used.

By fulfilling the condition that I1 is substantially equal to I2, it is ensured that the two connecting terminals A, B of the loop have a high input impedance with respect to the signal received from the transducer and within the frequency band thereof. However, since I1 is not strictly equal to I2, the difference I1–I2 of these currents is absorbed by resistor Ro. This resistor as well as the current difference I1–I2 determine the common mode D.C. potential at the terminals A, B of the transmission loop.

High-pass filter 17 provides D.C. decoupling and thereby eliminates the D.C. component of the electric signal provided by piezoelectric transducer 11, and provides t o reading circuit 12 a signal which is free of said component. The D.C. component just mentioned is the bias voltage Udc of the current loop. In the basic circuit diagram of FIG. 1, bias voltage Udc is represented as a voltage developing at the terminals of voltage source 27, which is a part of the equivalent circuit diagram of the transducer represented therein.

Differential amplifier stage 18 has a high input impedance which serves to reject the common mode potential (frame voltage) and to amplify the alternating signal Uac delivered by the piezoelectric transducer. Differential amplifier 18 is preferably an operational amplifier. The input of stage 18 is connected to the output of high-pass filter 17. The output (terminals X, Y) of stage 18 delivers a signal Uout to the input of reading circuit 12.

Figure 2:
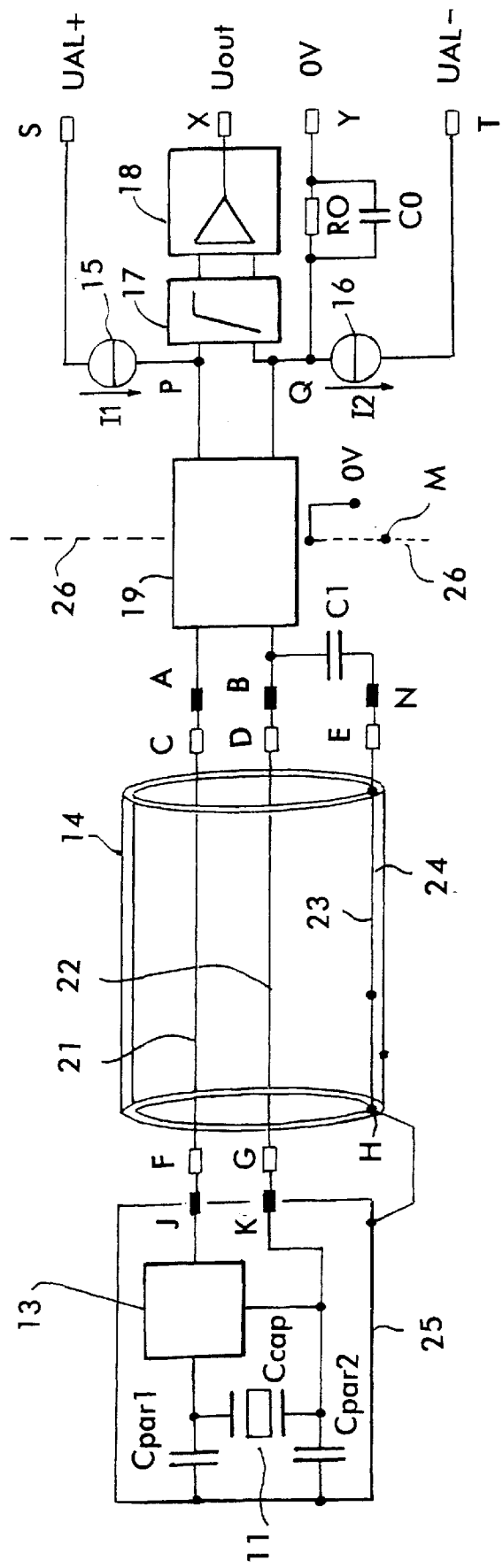
FIG. 2 shows a block diagram of a first embodiment of a system comprising an electronic interface circuit of the type represented in FIG. 1. In this figure, the connecting cable is of the twin-wire type and has a shield.
Figure 3:
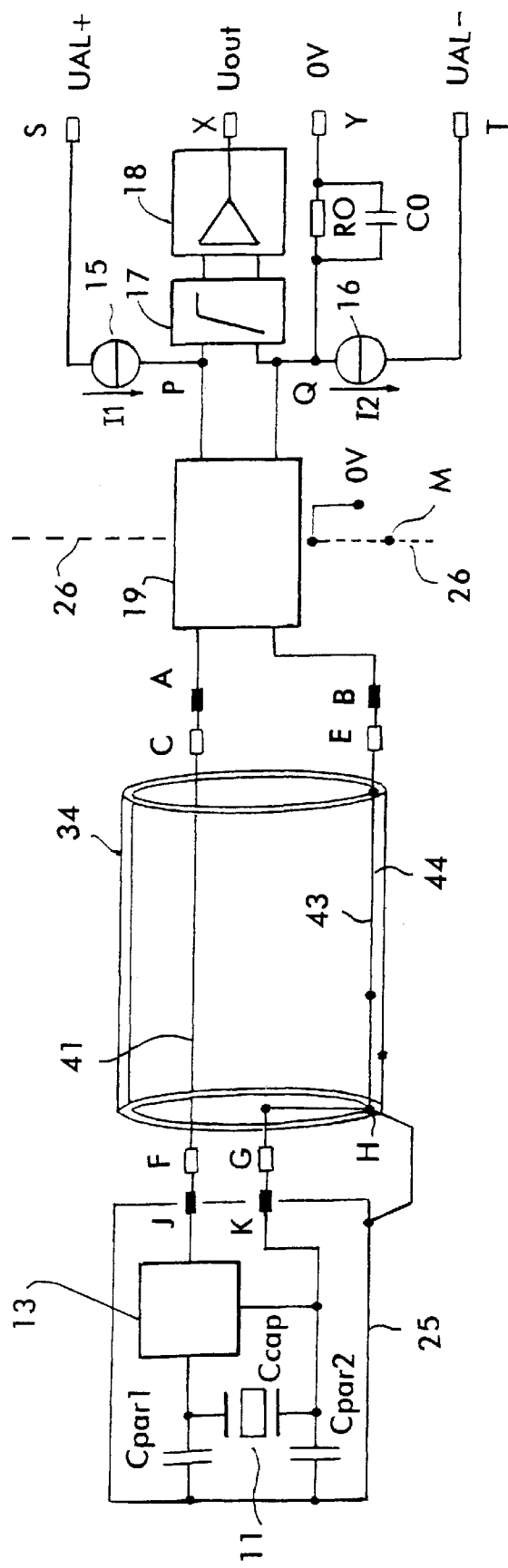
FIG. 3 shows a block diagram of a second embodiment of a system comprising an electronic interface circuit of the type represented in FIG. 1. In this figure, the connecting cable is of the single-wire type and has a shield, and the sensitive part of the transducer is insulated from its housing.
Figure 4:
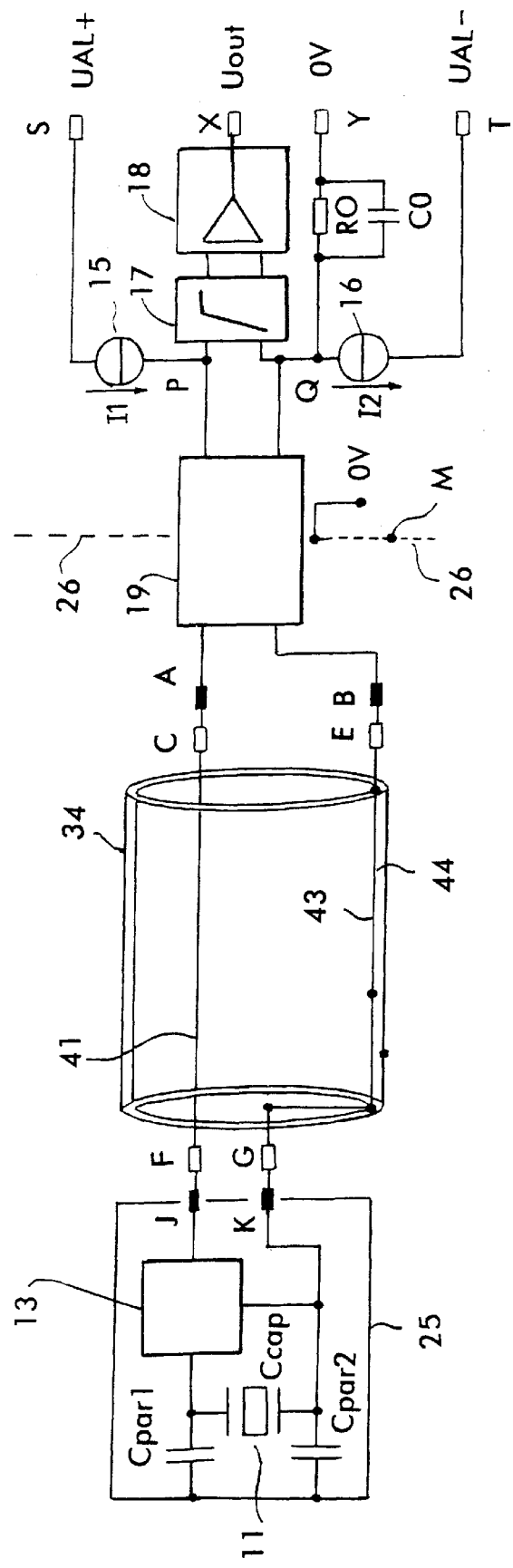
FIG. 4 shows a block diagram of a variant of the system represented in FIG. 3 with the difference that the sensitive part of the transducer is connected to its housing.

In preferred embodiments of an EIC according to the invention represented in FIGS. 2–4, the latter further comprises a filter 19 for the purpose of eliminating electromagnetic interferences, said filter 19 being inserted between terminals C, D of the second cable end and input terminals P, Q of the high-pass filter 17.

Figure 5:
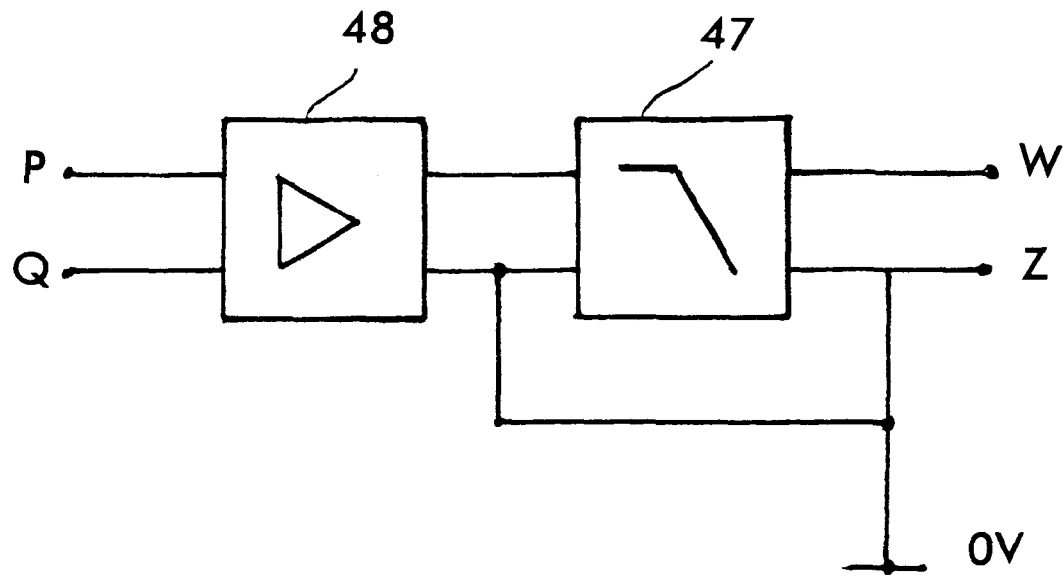
FIG. 5 shows a block diagram of an additional part added to the basic diagram of FIG. 1 allowing to obtain an additional function with the electronic interface circuit according to the invention.

FIG. 5 shows a block diagram of an additional part which may be added to the circuit represented by the basic circuit diagram of FIG. 1. This additional part comprises a differential amplifier 48 having a high input impedance, whose input is connected to terminals P and Q of the circuit diagram shown in FIG. 1. Differential amplifier 48 is followed by a low-pass filter 47 which serves to reject the signal component representing the physical value measured by piezoelectric transducer 11 and to retain and deliver to terminals W, Z a signal which corresponds only to the D.C. component of the signal, i.e. a signal corresponding to the bias voltage Udc of the loop.

By monitoring the output voltage of low-pass filter 47, it is possible to monitor the level of the D.C. voltage present between the two loop connecting terminals A, B (bias loop voltage Udc) and to detect a possible failure in the transmission loop, e.g. a malfunction with respect to the electric connection of the electronic interface circuit to piezoelectric transducer 11.

Figure 6:
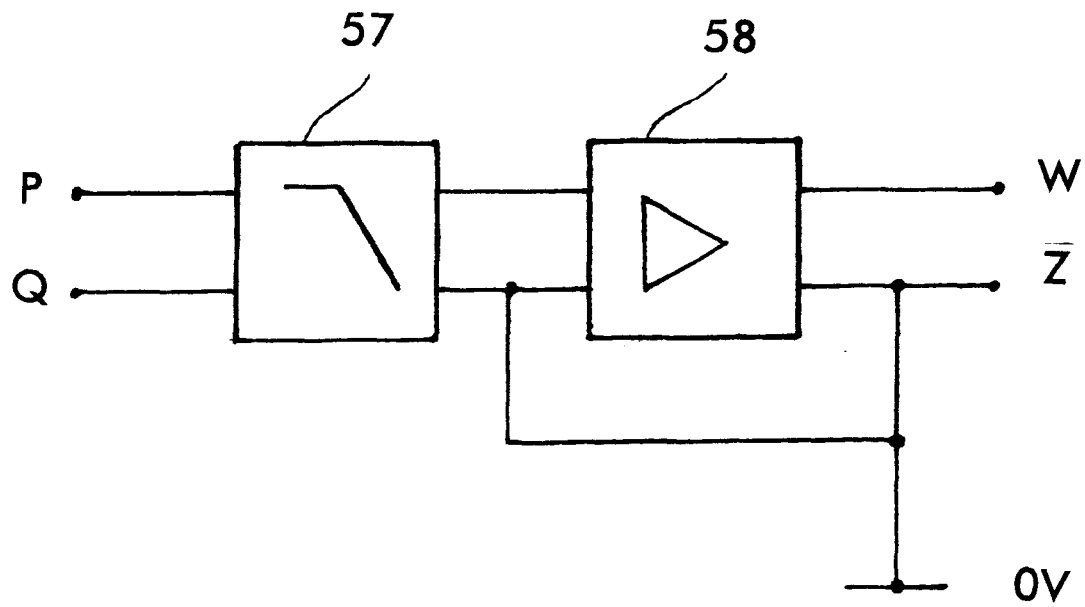
FIG. 6 shows a block diagram of an additional part which may be added to the basic diagram of FIG. 1 instead of the additional part represented in FIG. 5 in order to obtain an additional function with the electronic interface circuit according to the invention.

FIG. 6 shows a block diagram of an additional part which may be added to the basic diagram of FIG. 1 instead of the additional part represented in FIG. 5 in order to obtain an additional function with an electronic interface circuit according to the invention.

The additional part represented in FIG. 6 comprises a low-pass filter 57 and an amplifier stage 58. Low-pass filter 57 has a high input impedance and receives at its input an electric signal provided by transducer 11 via cable 14, 34. Low-pass filter 57 serves to eliminate the component of the signal provided by the transducer which corresponds to the physical value measured by the latter, and to deliver an output signal representing the D.C. component of said signal. The input of amplifier stage 58 is connected to the output of low-pass filter 57. The output signal of amplifier stage 58 allows to detect a malfunction with respect to the electrical connection between the transducer and the electronic interface circuit.

The use of an EIC according to the invention is illustrated by the following examples:

EXAMPLE 1

FIG. 2 shows a measuring chain where an EIC according to the invention performs two functions:

- it supplies a constant direct current to a piezoelectric transducer 11, and
- it pre-processes an electric signal provided by transducer 11 via an electronic circuit 13 integrated with the transducer. Electronic circuit 13 essentially comprises a current-fed voltage modulator 13. Instead of a voltage modulator, it is possible to use a current-fed charge/voltage converter. In a preferred embodiment, the voltage modulator, or the charge/voltage converter used instead thereof, is followed by an integrating stage.

In the example represented in FIG. 2, piezoelectric transducer 11 and electronic circuit 13 integrated therewith are insulated from housing 25 in which transducer 11 and its integrated electronic circuit 13 are enclosed. Capacitor Ccap shown next to transducer 11 in FIG. 2 represents the electric capacitance of the measuring element of the transducer itself. Cpar1 and Cpar2 represent stray capacities between the transducer and housing 25.

A cable 14 having two wires 21, 22 and a shield 23 covered with an insulation 24 is used for the connection of the EIC according to the invention (represented on the right side of the diagram of FIG. 2) to piezoelectric transducer 11 and electronic circuit 13 integrated therewith. Two terminals F, G at one end of cable 14 are connected to terminals J, K at the output of electronic circuit 13, and two corresponding terminals C, D at the opposite end of cable 14 are connected to terminals A, B of the EIC according to the invention.

The arrangement shown in FIG. 2 and the use of an EIC according to the invention in such an arrangement make it possible to obtain the following operating characteristics:

a) it is prevented that the presence of a common mode voltage (frame voltage) appearing between housing 25, which holds transducer 11, and housing 26, which holds the EIC according to the invention, generates an error voltage superposed to the measuring signal at the output of the circuit;

b) it is ensured that the shield of the connecting cable cannot conduct a current between housing 25 of the transducer and housing 26, whose voltage level defines the zero volt level of the EIC, and c) an advantageous behavior of the measuring chain with respect to electromagnetic interferences is provided.

EXAMPLE 2

FIG. 3 shows a measuring chain whose structure is similar to that according to FIG. 2 but where a cable 34 having a single wire 41 and a shield 43 covered by an insulation 44 is used for the connection of the EIC according to the invention (shown on the right side of the diagram of FIG. 3) to piezoelectric transducer 11 and electronic circuit 13 integrated therewith. Cable 34 is preferably an insulated coaxial cable.

The measuring chain represented in FIG. 3 also allows to obtain operating conditions a) and c) indicated above with respect to example 2, but characteristic b) is not obtained because a current Ishield can flow through the shield 43 of cable 34. This current amounts to Ishield=Uframe/Ro for low frequencies, and to Ishield=Uframe*Co*ω for high frequencies.

EXAMPLE 3

FIG. 4 shows a measuring chain whose structure is almost identical to that according to FIG. 3 but where terminal K of electronic circuit 13 integrated with transducer 11 is connected to housing 25. The measuring chain represented in FIG. 4 allows the same operational characteristics as the measuring chain represented in FIG. 3.

Determining the parameters of an EIC according to the invention

The equations and relationships which define the operation of the electronic interface circuit (EIC) according to the invention are as follows:

The voltage Ucap generated by electronic circuit 13 integrated with the transducer is equal to:

$$Ucap=Uac+Udc \tag{1.1}$$

The D.C. current Iro flowing through Ro is equal to:

$$Iro=I1-I2 \tag{1.2}$$

The common mode D.C. voltage Uro across Ro on account of the inequality of the currents I1 and I2 is equal to:

$$Uro=Ro*(I1-I2) \tag{1.3}$$

The voltage Uro should be as low as possible in order to be able to process the maximum common mode voltage Ucmpeak (A.C. voltage). The value of Ucmpeak is dictated by:

- the maximum value of the bias voltage Udcmax,
- the minimum value of the supply voltages UAL+, UAL−,
- the maximum voltage drop (Ui1, Ui2) at the terminals of the D.C. current sources,
- the maximum common mode D.C. voltage Uromax caused by the dissymmetry of I1−I2 and by the peak A.C. signal generated by the transducer (Uacpeak).

It is required that $$Uromax+Uacpeak+Udcmax+Ucmpeak \leq (UAL+)-Ui1 \tag{1.4}$$

and $$|Uromax|+|Uacpeak|+|Ucmpeak| \leq |UAL-|-|Ui2| \tag{1.5}$$

From equations (1.4) and (1.5) it follows that:

$$Ucmpeak<(UAL+)-Ui1-Uacpeak-Udcmax-Uromax \tag{1.6}$$

and $$|Ucmpeak| \leq |UAL-|-|Ui2|-|Uromax|-|Uacpeak| \tag{1.7}$$

while $$Uromax=\Delta Imax*Ro \tag{1.8}$$

$$\Delta Imax=(I1-I2)max \tag{1.9}$$

The cut-off frequency of high-pass filter 15 which serves for decoupling the D.C. component (bias voltage of the current loop) is:

$$Fchp = \frac{1}{2} * \pi * \tau \quad (1.10)$$

$$\tau = R*C = \text{time constant of the high-pass filter} \quad (1.11)$$

The gain of high input impedance differential amplifier 18 is:

$$G = Uout/Uac \quad (1.12)$$

What is claimed is:

1. An electronic circuit serving as an interface between a piezoelectric transducer and a circuit for processing a measuring signal provided by said transducer, said electronic interface circuit serving for providing a constant direct current to said piezoelectric transducer, and for preprocessing an electric signal provided by the transducer via a voltage modulator, said electronic interface circuit being connected to said voltage modulator by a cable having two terminals at each end, the two terminals at a first end of the cable being connected to the output of the voltage modulator and the two terminals at a second end of the cable being connected to said electronic interface circuit, wherein said electronic interface circuit comprises (a) a first direct current source for providing a first constant current to said transducer through an electric current loop;

(b) a second direct current source for absorbing a second constant current returning from said transducer to said electronic circuit through said loop while said transducer is supplied with said first current;

(c) at least one passive element allowing to absorb the difference between said first constant current and said second constant current.

2. An electronic circuit according to claim 1, wherein said at least one passive element is an impedance which is connected in parallel between the current input terminal of said second direct current source and the ground of the electronic interface circuit, said impedance being composed of an electric resistor connected in parallel to a capacitor, said electric resistor being adapted for absorbing an electric current which is equal to the difference between said first constant current and said second constant current.

3. An electronic circuit according to claim 1, further comprising (d) a high-pass filter for receiving an electric signal provided by said transducer via said cable, for eliminating the D.C. component of said signal, and for delivering an output signal which is free of said component, and (e) a first differential amplifier stage having a high input impedance, the input of said stage being connected to the output of said high-pass filter.

4. An electronic circuit according to claim 3, further comprising a filter for eliminating electromagnetic interferences, said filter being inserted between the terminals of said second cable end and the input terminals of said high-pass filter.

5. An electronic circuit according to claim 3, comprising (a) a second differential amplifier stage having a high input impedance and whose input receives an electric signal provided by said transducer via said cable, and (b) a low-pass filter whose input is connected to the output of said second differential amplifier stage, said low-pass filter serving to eliminate the component of said signal which corresponds to the physical value measured by the transducer, and to deliver an output signal representative of the D.C. component of said signal.

6. An electronic circuit according to claim 1, comprising (a) a low-pass filter having a high input impedance and whose input receives an electric signal provided by said transducer via said cable, and which serves to eliminate the component of the signal provided by the transducer which corresponds to the physical value measured by the latter, and to deliver an output signal representative of the D.C. component of said signal, and (b) an amplifier stage whose input is connected to the output of said low-pass filter and whose output signal allows to detect a malfunction with respect to the connection between the transducer and the electronic interface circuit.

\* \* \* \* \*